(12) United States Patent
Parmee

(10) Patent No.: US 6,385,284 B1
(45) Date of Patent: May 7, 2002

(54) RADIATION MONITORING OF A PHYSICAL PROPERTY OF A MATERIAL

(75) Inventor: Richard John Parmee, Ashwell (GB)

(73) Assignee: Safeline AVS Limited, Ashwell (GB)

( * ) Notice: Subject to any disclaimer, the term of this patent is extended or adjusted under 35 U.S.C. 154(b) by 0 days.

(21) Appl. No.: 09/743,351
(22) PCT Filed: Jul. 8, 1999
(86) PCT No.: PCT/GB99/02171
§ 371 Date: Jan. 5, 2001
§ 102(e) Date: Jan. 5, 2001
(87) PCT Pub. No.: WO00/03236
PCT Pub. Date: Jan. 20, 2000

(30) Foreign Application Priority Data

Jul. 8, 1998 (GB) .............................................. 9814701

(51) Int. Cl.$^7$ .............................................. G01B 15/02
(52) U.S. Cl. ........................... 378/54; 378/207; 378/51
(58) Field of Search ............................. 378/54, 57, 53, 378/207, 98.4, 51

(56) References Cited

U.S. PATENT DOCUMENTS 5,327,476 A * 7/1994 Kemner ...................... 378/98.4
5,974,111 A * 10/1999 Krug et al. .................... 378/57

* cited by examiner

Primary Examiner—David V. Bruce
Assistant Examiner—Pamela R. Hobden
(74) Attorney, Agent, or Firm—Fildes & Outland, P.C.

(57) ABSTRACT

Apparatus and assembly for and associated method of monitoring a physical property of a material, such as the specific gravity of a processed meat product of the density, and hence weight, of tobacco in a cigarette rod, comprising: means (19) arranged to direct radiation (30) into a material having a physical property to be monitored; first sensing means (23) arranged to sense levels of residual measurement radiation passing from the irradiated material and to provide respective measurement signals representative of the sensed levels of residual measurement radiation; reference means (18) which is arranged to be located in the path of the radiation (30), optionally adjacent or within the material whose physical property is to be monitored, and which has radiation absorption characteristics corresponding to predetermined low and/or high radiation absorption characteristics of the material whose physical property is to be monitored; second sensing means (22) arranged to sense levels of residual reference radiation passing from said irradiated reference means and to provide reference signals representative of said sensed levels of residual reference radiation; and means (130) arranged to process the measurement and reference signals, to provide interpolated measurement signals which are corrected to take into account any variable operating parameters of the apparatus and which are representative of the actual monitored physical property. The invention also provides a method of calibrating the apparatus on an on-going basis.

23 Claims, 1 Drawing Sheet

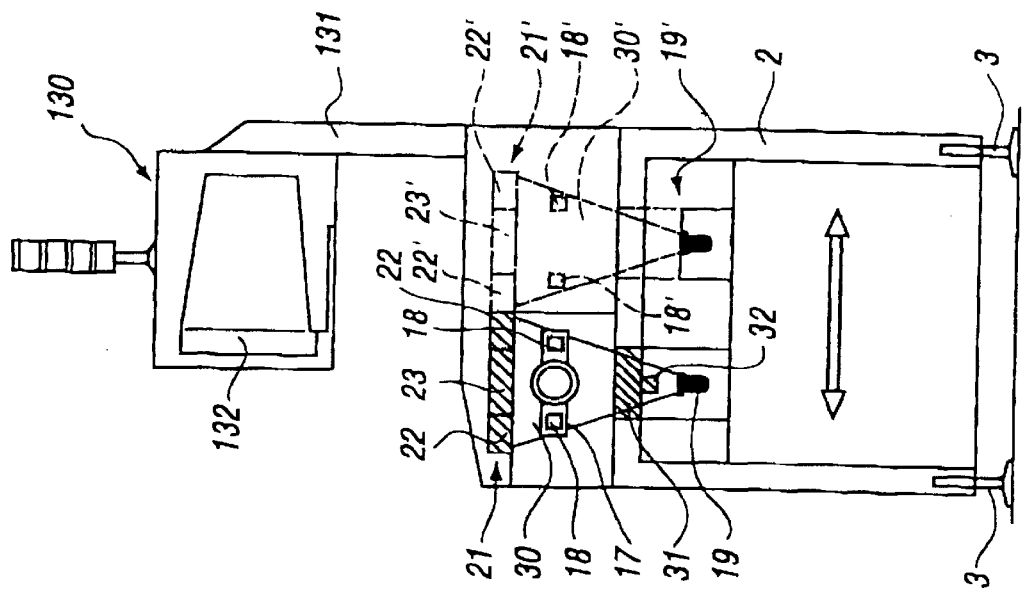
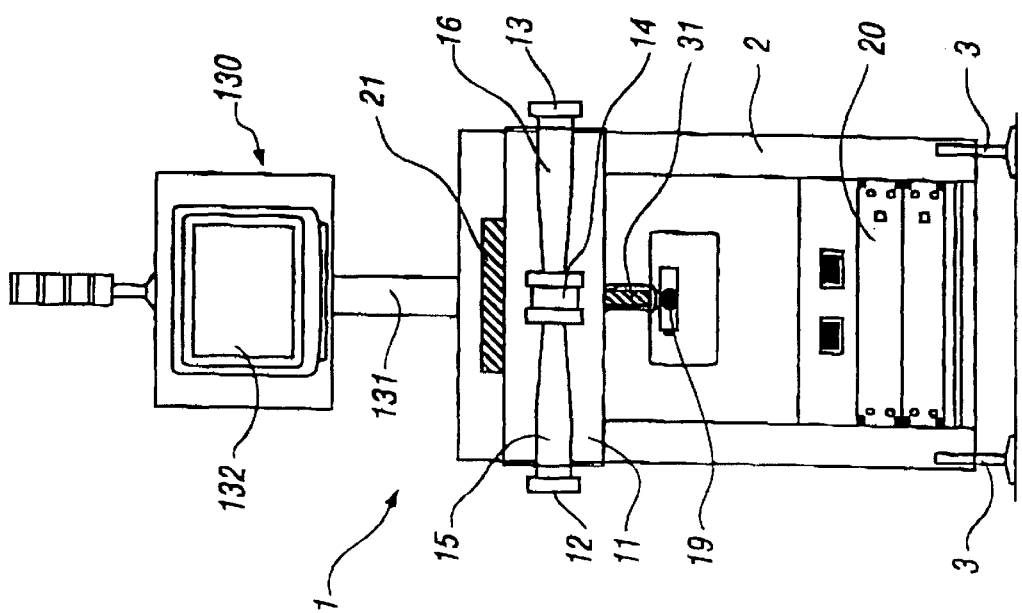
FIG 1
FIG 2

RADIATION MONITORING OF A PHYSICAL PROPERTY OF A MATERIAL

DESCRIPTION

This invention relates to the monitoring of a physical property of a material, such as the specific gravity (density) of a manufactured meat product or the density, and hence weight, of tobacco in a "cigarette rod" of constant cross-sectional area, using a penetrative or diffractive radiation, for example an X-ray beam, and measuring its absorption by the material whose physical property is to be measured, to determine such property.

The invention has particular application in the meat processing industry, as well as other product processing industries, for example, the tobacco, pharmaceutical and plastics processing industries.

Typically, a material of which a physical property, such as the specific gravity, is to be monitored, is placed in the path of a beam of radiation, for example, an X-ray beam, to produce a signal at a sensor or an array of sensors representative of the value of the physical property which is dependent upon the amount of radiation absorbed by the product and, hence, the residual amount of radiation received by the sensor(s).

In the meat processing industry, the monitoring of the specific gravity of a meat product slurry or emulsion of various particle sizes can be used to determine changes in the proportion of fat within the product. Because the difference in specific gravities gives rise to only a very small signal variation using conventional techniques, it has been found necessary to develop a technique for monitoring the specific gravity of processed meat products to a greater accuracy than previously.

In the tobacco industry, weight control of cigarettes has been determined traditionally by monitoring the beta ray absorption of the cigarette at the point where it has been formed into a "rod". This technique forms part of a closed loop system for maintaining consistency in the weight of the cigarettes, which is particularly important in view of the high cost of tobacco products. At present, the application of radioactive sources, such as that for generating beta rays, is becoming increasingly undesirable due to the regulatory considerations associated with the handling and disposal of such sources.

In the pharmaceutical industry, similar monitoring techniques are used for the accurate determination of the weight of dispensed powder drugs or tablets in containers, such as blister packs.

Also, in the medical industry, similar monitoring techniques are used for the accurate determination of quantities of dressings in packs.

Further, in the food industry, similar monitoring techniques are used for the accurate determination of product presence and/or mass.

However, in all the present radiation absorption monitoring techniques, the resulting signal(s) produced by the sensor(s) due to the receipt thereby of the residual radiation which has not been absorbed by the product, is influenced by several operating parameters which can vary indeterminately during the monitoring process. Such variable operating parameters include, in the case of radiation absorption monitoring techniques, the acceleration voltage applied to the radiation generator, for example, an X-ray beam generator, the radiation beam current of the generator and, in the vast majority of cases, changes in the ambient temperature of the monitoring environment.

These variations in such operating parameters, as well as others, during the monitoring process result in inaccurate monitoring measurements, which is undesirable if the physical property of the product is to be determined accurately.

Generally, it is difficult to stabilise some or all of these parameters to a degree which is sufficient to provide the required accuracy of physical property monitoring.

Several solutions have been proposed to the problems associated with the monitoring of a property of a material. For example, Johnson, in his United State patent (U.S. Pat. No. 4,504,963), proposes a system for analysing meat in which a sample of meat is placed in a sample container which is irradiated with X-rays, the attenuated beam being detected and compared with a previously determined calibration. The signal of the attenuated beam is related to the fat content of the meat and thereby provides a measure of the fat content of the meat.

Hauni Mascinenbau AG in their European patent (EP0790006) propose an "on-line" analysis method in which X-rays are utilised to monitor the density of a cigarette rod as it passes the apparatus. It is taught that an absolute measure of tobacco density nay be effected by continuously monitoring the dark signal of a detector element, the fill signal (un-attenuated beam) with a detector element, and the beam strength after passage through slices of the cigarette rod. The dark signal and fill signal are used to correct the readings of the other detector elements which monitor the beam through respective slices of the cigarette rod. In this fashion the apparatus provides an absolute measure of the density of tobacco.

Molins PLC, in their International patent application (WO 97/29654), disclose further apparatus for monitoring tobacco density in a cigarette rod in which a reference sample, a "dummy" cigarette, is irradiated with X-rays and the signal derived therefrom is used to control the X-ray emitter so as to ensure a constant output therefrom. By ensuring such constant output, the signal which is derived from the detector which measures the beam strength following passage of the X-rays through the cigarette rod is related to the density of the tobacco in the rod.

Accordingly, it is an object of the present invention to provide apparatus and an associated method, which overcomes, or at least substantially reduces, the disadvantages discussed above in relation to known radiation absorption techniques for monitoring a physical property of a manufactured product.

Thus, a first aspect of the invention resides in dual calibration apparatus for "on-line" or continuous monitoring of a physical property of a material, such as the specific gravity of a processed meat product or the density, and hence weight, of tobacco in a cigarette rod, the apparatus comprising:

(a) means arranged to direct radiation into a material having a physical property to be monitored;

(b) first sensing means arranged to sense levels of residual measurement radiation passing from the irradiated material and to provide respective measurement signals representative of said sensed levels of residual measurement radiation;

(c) reference means which is arranged to be located in the path of the radiation, optionally adjacent or within the material whose physical property is to be monitored, and which has radiation absorption characteristics corresponding to predetermined low and high radiation absorption characteristics of the material whose physical property is to be monitored:

(d) second sensing means arranged to sense levels of residual reference radiation passing from said irradiated reference means and to provide reference signals representative of said sensed levels of residual reference radiation, (e) means arranged to process the measurement and reference signals, to provide interpolated measurement signals; and characterised in that, said reference means comprises a pair of spaced reference standards, a low radiation absorption characteristic standard whose absorption characteristic corresponds to a minimum level of the physical property to be monitored and a high radiation absorption characteristic standard whose absorption characteristic corresponds to a maximum level of the physical property to be monitored, the interpolated results being corrected to take into account any variable operating parameters of the apparatus and being representative of the actual monitored physical property.

In accordance with a second aspect of the invention, there is provided a method of "on-line-" or continuous monitoring a physical property of a material, such as the specific gravity of a processed meat product or the density, and hence weight, of the tobacco in a cigarette rod, which method comprises;

directing radiation into a material having a physical property being monitored;

sensing levels of residual measurement radiation passing from the irradiated material;

providing measurement signals representative of said sensed levels of residual measurement radiation;

locating in the path of the radiation, optionally adjacent or within the material whose physical property is being monitored, reference means having radiation absorption characteristics corresponding to predetermined low and/or high radiation absorption characteristics of the material whose physical property is to be monitored;

sensing the level of residual reference radiation passing from said irradiated reference means;

providing reference signals representative of said sensed levels of residual reference radiation;

processing the measurement and reference signals to provide interpolated measurement signals; and characterised in that, said reference means comprises a pair of spaced reference standards, a low radiation absorption characteristic standard whose absorption characteristic corresponds to a minimum level of the physical property to be monitored and a high radiation absorption characteristic standard whose absorption characteristic corresponds to a maximum level of the physical property to be monitored, and correcting the interpolated results to take into account any sensed variation of the operating parameters and thereby representing the actual monitored physical property.

In both aspects of the invention defined above, the radiation employed is preferably X-rays generated by a suitable X-ray source which, in the preferred embodiment to be described hereinbelow, provides a diverging X-ray beam directed at and into the material, as well as at and into the reference means.

Also, in the case of the inventive apparatus, the first sensing means for sensing levels of residual measurement radiation passing from the irradiated material and for providing measurement signals representative of those sensed residual measurement radiation levels, may be of any suitable form. In the preferred embodiment to be described hereinbelow, such first sensing means may comprise an X-ray detector capable of providing measurement signals representative of the residual measurement levels of X-rays received thereby from the irradiated material whose physical property is to be monitored.

Again, and in the case of the inventive apparatus defined above, the pair of spaced reference elements indicated above, may be of any suitable form, for example, an X-ray detector capable of providing reference signals representative of the levels of residual reference radiation received thereby.

The two spaced reference elements may each have its own second sensing means, possibly incorporated with the first sensing means, for example in a single array. In such a case, respective measurement and reference signals from all three sensing means can be processed, by suitable processing means, to provide interpolated measurement signals representative of the actual physical property of the material in question. In this manner, any operating parameters of the inventive apparatus, assembly and method which vary during the monitoring process and which can influence, in an undesirable manner, the sensed levels of residual measurement radiation from the material are "calibrated out" using the reference signals, to provide a true value for the monitored physical property of the material.

At least insofar as the parameter of the material to be monitored is concerned, the radiation absorption characteristic of the material of the reference means such as the reference elements to be discussed hereinbelow, is preferably very close to or substantially the same as that of the material whose physical property is to be monitored.

Periodically, the pair of spaced reference elements, whose radiation absorption characteristics correspond respectively to predetermined low and high radiation absorption characteristics of the material whose physical property is to be or is being monitored, can be calibrated absolutely. For example, in the inventive monitoring apparatus, the radiation source and at least the second sensing means can be moved from the vicinity of the material chamber to a position where pre-certified calibration elements can be moved into the path of the radiation, for example, into the X-ray beam, between that source and the sensor means. Such calibration elements are certified to correspond to predetermined low and high percentage tolerance levels of the radiation absorption characteristics of the material in question and are used to calibrate out any medium or long term drift which may have occurred in the reference means located in the path of the radiation during the monitoring process. This arrangement may also be used to calibrate the linearity of the monitoring apparatus and assembly, particularly the signal processing means thereof.

Additionally or alternatively, such calibration may be facilitated by a series of certified references which can be indexed through the X-ray or other radiation beam by means of a motorised mechanism Also, such calibration can be programmed to occur at predetermined time intervals.

Preferably, the geometry of at least those components of the inventive apparatus and assembly involved in the monitoring method is symmetrical or substantially so, in order to maintain uniform radiation of the sensing and reference means.

Further, it is to be understood that although X-ray radiation is preformed, other types of suitable radiation may be employed in the inventive apparatus, assembly and method described above.

In order that the invention may be more fully understood, a preferred embodiment of monitoring apparatus in accordance with the first aspect of the invention for monitoring the fat content of a processed meat product, will now be described by way of example and with reference to the accompanying drawing in which:

FIG. 1 to a front elevation of a monitoring unit incorporating the inventive apparatus; and FIG. 2 is a side elevation of the unit of FIG. 1, showing respective operating and calibrating positions of some components of the apparatus.

Referring firstly to FIG. 1 of the drawing, a unit, indicated generally at 1, for monitoring the specific gravity of a processed meat product which is dependent upon the variable fat content of the product, comprises a generally rectangular support cabinet 2 mounted upon four adjustable legs 3 at respective lower corners thereof. Mounted transversely of the upper region of the cabinet 2 is a manifold indicated generally at 11 and comprising an inlet 12, an outlet 13, a chamber 14 which is intermediate the inlet 12 and outlet 13 and which communicates therewith via respective conduits 15, 16.

A processed meat product in the form of a meat emulsion can be pumped through the manifold 11 from left to right when the inlet 12 is connected to the outlet (not shown) of a meat processing machine.

The internal cross section of the chamber 14 is substantially uniform, such that the meat emulsion being pumped therethrough is also of substantially uniform cross section.

Located on respective opposed front and rear sides of the chamber 14 is a pair of sub-chambers 17 in each of which is mounted a reference element 18, as shown in FIG. 2 and as described in more detail hereinbelow.

Mounted in the support cabinet 2 below the manifold 11 but in-line with the chamber 14 and sub-chambers 17, is an X-ray source 19. The power supply, and associated control equipment, for the X-ray source 19 is mounted in the lower region of the cabinet 2, as shown generally at 20 in FIG. 1.

Mounted in the cabinet 2 above the manifold 15 but in-line with the chamber 14 and sub-chambers 17, as well as the X-ray source 19, is an X-ray sensor array indicated generally at 21 and having respective outer portions 22 and an inner portion 23 for detecting X-rays, as will also be described in more detail hereinbelow.

In operation of the unit 1, the inlet 12 of the manifold 11 is connected to the outlet of meat processing equipment and the outlet 13 of the manifold 11 is connected to any suitable equipment for further processing or packaging of the meat emulsion.

The emulsion is pumped, from left to right, through the manifold 11 and the X-ray source 19 directs a diverging X-ray beam, as shown at 30 in FIG. 2, into the chamber 14 through which the emulsion is being pumped and through the sub-chambers 17 in which the reference elements 18 are mounted.

The reference elements 18 are made of any suitable, stable, non-hygroscopic material, and have a radiation absorption characteristic which corresponds substantially to predetermined low and high radiation absorption characteristics of the meat emulsion being pumped through the chamber 14.

The inner, intermediate portion 23 (first sensing means) of the X-ray sensor array 21 detects the levels of residual measurement X-rays passing through and from the chamber 14, and hence through and from the emulsion, to provide respective measurement signals representative of those sensed residual measurement X-ray levels.

Similarly, the outer portions 22 (secondary securing means) of the X-ray sensor array 21 detect levels of residual reference X-rays passing through and from respective reference elements 18, to provide reference signals representative of those sensed levels of residual reference X-rays.

Processing means (not shown) located within a housing 130 supported above the cabinet 2 by a leg 131 through which cables from the various electrical components of the assembly extend to the processor, then processes the measurement and reference signals, to provide interpolated measurement signals which are representative of the specific gravity of the meat emulsion within the chamber 14 and which are corrected, using the reference signals from the respective reference elements 22, to take into account any variable operating parameters of the assembly, for example, the acceleration voltage applied to the X-ray source 19, the X-ray beam. current of the generator 19, as well as changes in the ambient temperature of the monitoring environment.

These corrected, interpolated measurement signals, which are representative of the actual monitored specific gravity of the meat emulsion, are also representative of the fat content of the emulsion.

A video screen 132 is provided in the front wall of the housing 130, for displaying the corresponding fat contents of the meat emulsion whose specific gravity is being monitored.

From time to time, the reference elements 18 need to be re-calibrated absolutely and this is carried out by moving the X-ray sensor array 21 and X-ray source 19 in unison from their operating, monitoring position at the front of the unit 1, as shown in whole lines in FIG. 2, to a calibration position at the rear of the unit 1, as shown in dashed lines in that FIG. 2.

Additionally or alternatively, such re-calibration may be facilitated by a series of certified references, as shown generally at 31 in FIGS. 1 and 2, which can be indexed through the X-ray beam 30 by means of a motorised mechanism indicated diagrammatically at 32.

In the calibration position, the X-ray sensor array is indicated generally at 21', with respective outer and inner portions thereof being shown at 22' and 23'. The diverging X-ray beam is shown at 30', whilst the X-ray source is shown at 19'.

Pre-certified calibration elements 18', corresponding to the reference elements 18, are moved into the path of the X-ray beam 30', between the X-ray source 19' and the X-ray sensor array 21'. These calibration elements 18' are certified to correspond to absolutely predetermined low and high percentage tolerance levels of the radiation absorption characteristics of the meat emulsion and are used to calibrate out any medium or long term drift which may have occurred in the reference elements 18 during the monitoring process. As indicated above, this arrangement may also be used to calibrate the linearity of the monitoring apparatus and assembly, for example, the measurement and reference signal processing means.

Such re-calibration can be programmed to occur at pre-determined time intervals.

Also, the assembly can be arranged to control automatically the flow of meat emulsion through the monitoring manifold 11, so that the flow of meat emulsion is inhibited or terminated during re-calibration, thereby assuring that all the processed meat product emulsion is monitored for fat content.

It is to be appreciated that the inventive apparatus, assembly and method may also be used for monitoring physical properties of other products, with a view to removing contaminants therefrom, particularly solid contaminants, such as metal, stone, glass, bone and various types of plastics material.

In a modification of the inventive apparatus, assembly and method, the first and second radiation sensing means, such as the X-ray sensing array 21 of the embodiment described above, may be mounted upon and in close thermal contact with an isothermal block which is maintained at a constant temperature, thereby substantially removing any temperature variations from that/those components of the inventive apparatus and/or assembly, which might otherwise have a deleterious effect on the monitoring results. In addition to assisting in the maintenance of the monitoring accuracy of the apparatus and method, any input amplifier of the processing means and/or its associated circuitry may also be coupled thermally to the isothermal block.

Additionally or alternatively, the temperature of the sensing means and/or the monitoring chamber may be monitored and used to provide suitable correction signals to the measurement signals.

Although the embodiment described above employs X-rays as a penetrative and absorptive form of radiation, other forms of such radiation may be used, as may forms of penetrative diffractive radiation.

It is to be appreciated that physical properties of other material, such as the density, arid hence weight, of tobacco in cigarette rods, may also be monitored using the inventive method and apparatus.

What is claimed is:

1. Dual calibration apparatus (1) for "on-line" or continuous monitoring of a physical property of a material, such as the specific gravity of a processed meat product or the density, and hence weight, of tobacco in a cigarette rod, the apparatus comprising:

(a) means (19) arranged to direct radiation into a material having a physical property to be monitored, (b) first sensing means (23) arranged to sense levels of residual measurement radiation passing from the irradiated material and to provide respective measurement signals representative of said sensed levels of residual measurement radiation;

(c) reference means (18) which is arranged to be located in the path of the radiation, optionally adjacent or within the material whose physical property is to be monitored, and which has radiation absorption characteristics corresponding to predetermined low and high radiation absorption characteristics of the material whose physical property is to be monitored;

(d) second sensing means (22) arranged to sense levels of residual reference radiation passing from said irradiated reference means and to provide reference signals representative of said sensed levels of residual reference radiation;

(e) means arranged to process the measurement and reference signals, to provide interpolated measurement signals; and characterised in that, said reference means (18) comprises a pair of spaced reference standards, a tow radiation absorption characteristic standard whose absorption characteristic corresponds to a minimum level of the physical property to be monitored and a high radiation absorption characteristic standard whose absorption characteristic corresponds to a maximum level of the physical property to be monitored, the interpolated results being corrected to take into account any variable operating parameters of the apparatus (1) and being representative of the actual monitored physical property.

2. Apparatus (1) according to claim 1, wherein said first sensing means (23) comprises a radiation detector capable of providing measurement signals representative of the residual measurement levels of radiation received thereby from the irradiated material whose physical property is to be monitored.

3. Apparatus (1) according to claim 1 or 2, wherein said second sensing means (22) comprises sensing means for each of the pair of spaced reference elements (18).

4. Apparatus (1) according to any of claim 1, 2 or 3, wherein said first and second sensing means (22; 23) are provided in a single array (21).

5. Apparatus (1) according to any preceding claim, wherein said reference means (18) comprises a material whose radiation absorption characteristic is very close to or substantially the same as that of the material whose physical property is to be monitored.

6. Apparatus (1) according to any preceding claim, wherein said radiation direction means comprises an X-ray source (19).

7. Apparatus (1) according to any preceding claim, wherein said first and second sensing means (22; 23) comprises an X-ray detector.

8. Apparatus (1) according to any preceding claim, wherein said radiation direction means (19) is arranged to provide a diverging beam of radiation (30) to be directed at and into the material whose physical property is to be monitored.

9. Apparatus (1) according to any preceding claim, wherein the geometry of at least those components of the apparatus associated with the monitoring of the material's physical property, is substantially symmetrical, to maintain uniform radiation of said reference and sensing means.

10. Apparatus (1) according to any preceding claim further comprising a chamber (14) arranged to accommodate the material having a physical property to be monitored, the radiation being arranged to be directed into the chamber (14) and, hence, into the material accommodated therein and having a physical property to be monitored.

11. Apparatus (1) according to claim 10, wherein the chamber (14) comprises a body of substantially uniform internal cross-section.

12. Apparatus (1) according to any preceding claim, wherein the material is arranged to be conveyed passed the radiation (30).

13. A method of "on-line" or continuous monitoring a physical property of a material, such as the specific gravity of a processed meat product or the density, and hence weight, of the tobacco in a cigarette rod, which method comprises;

directing radiation (30) into a material having a physical property being monitored;

sensing levels of residual measurement radiation passing from the irradiated material, providing measurement signals representative of said sensed levels of residual measurement radiation;

locating in the path of the radiation (30), optionally adjacent or within the material whose physical property is being monitored, reference means (18) having radiation absorption characteristics corresponding to predetermined low and/or high radiation absorption characteristics of the material whose physical property is to be monitored;

sensing the level of residual reference radiation passing from said irradiated reference means (18);

providing reference signals representative of said sensed levels of residual reference radiation;

processing the measurement and reference signals to provide interpolated measurement signals; and characterised in that, said reference means (18) comprises a pair of spaced reference standards, a low radiation absorption characteristic standard whose absorption characteristic corresponds to a minimum level of the physical property to be monitored and a high radiation absorption characteristic standard whose absorption characteristic corresponds to a maximum level of the physical property to be monitored, and correcting the interpolated results to take into account any sensed variation of the operating parameters and thereby representing the actual monitored physical property.

14. A method according to claim 13, wherein the radiation (30) is directed into the material whose physical property is being monitored as a diverging bean.

15. A method according to claim 13 or 14, wherein the levels of residual measurement radiation are sensed by a radiation detector (21) providing measurement signals representative of the residual measurement levels of radiation received thereby from the irradiated material whose physical property is being monitored.

16. A method according to any of claim 13, 14 or 15, wherein the level of residual reference radiation passing from the pair of irradiated spaced reference elements (18), is sensed by respective ones of a pair of sensing means (22).

17. A method according to any of claims 13 to 16, wherein said reference means (18) is provided by a material whose radiation absorption characteristic is very close to or substantially the same as the material whose physical property is being monitored.

18. A method according to any of claims 13 to 17, wherein the radiation (30) is X-ray radiation.

19. A method of calibrating said reference means of the apparatus (1) according to any of claims 1 to 12, which method comprises locating between a or the radiation source (19) and at least said second sensing means (22) at least one pre-certified calibration element (18') certified to correspond to absolutely predetermined low and high percentage tolerance levels of the radiation absorption characteristic of the material whose physical property is to be monitored, generating a signal to correspond to radiation passing from said at least one pre-certified calibration element (18') and employing that signal to calibrate out any medium or long term drift in said reference means (18).

20. A method according to claim 19, wherein calibration of said reference means is programmed to run at predetermined time intervals.

21. A method according to claim 19 or 20, wherein calibration is carried out remote from the operational monitoring position.

22. A method according to claim 19, 20 or 21, wherein calibration is carried out using a series of certified references (18') indexed through the path of the radiation (30).

23. A method according to claim 22, wherein indexing of the series of certified references (18') is effected by a motorised mechanism.

* * * * *